(12) United States Patent
Pfaller

(10) Patent No.: US 7,001,751 B1
(45) Date of Patent: Feb. 21, 2006

(54) PYRF GENE AND THE UTILIZATION THEREOF

(75) Inventor: Rupert Pfaller, München (DE)

(73) Assignee: Consortium für elektrochemische Industrie GmbH, Munich (DE)

(*) Notice: Subject to any disclaimer, the term of this patent is extended or adjusted under 35 U.S.C. 154(b) by 564 days.

(21) Appl. No.: 10/031,547

(22) PCT Filed: Jun. 29, 2000

(86) PCT No.: PCT/EP00/06091

§ 371 (c)(1),
(2), (4) Date: Jan. 18, 2002

(87) PCT Pub. No.: WO01/07620

PCT Pub. Date: Feb. 1, 2001

(30) Foreign Application Priority Data

Jul. 22, 1999 (DE) ................. 199 34 408

(51) Int. Cl.
*C12N 9/10* (2006.01)
*C12N 15/00* (2006.01)
*C12N 1/20* (2006.01)
*C12P 21/04* (2006.01)
*C07H 21/04* (2006.01)

(52) U.S. Cl. .............. 435/193; 435/6; 435/252.3; 435/320.1; 435/254.11; 435/71.1; 435/69.1; 435/440; 435/183; 536/23.1; 536/23.2; 536/23.74

(58) Field of Classification Search ......... 435/193, 435/440, 252.3, 320.1, 254.11, 71.1, 6, 69.1; 536/23.2, 23.1, 23.74; 530/350
See application file for complete search history.

(56) References Cited

FOREIGN PATENT DOCUMENTS

| DE | 19814853 | 10/1999 |
|---|---|---|
| EP | 0570096 | 11/1993 |
| WO | 9308272 | 4/1993 |
| WO | 9855628 | 12/1998 |

OTHER PUBLICATIONS

Rasmussen et al. The PYR1 gene of the plant pathogenic fungus Colletotrichum graminicola: selection by intraspecific complementation and sequence analysis. Mol Gen Genet. Oct. 1992;235(1):abstact.*
Rasmussen et al. NCBI Accession No. S47907.*
English Derwent Abstract AN corresp. to WO 98 55628.
Rsamussen Jack B. et al., Molecular & General Genetics, vol. 235, No. 1, 1992, pp. 74-80.
English Derwent Abstract AN 1999-633742 [54] corresp. to DE 198 14853 A1.
English Derwent Abstract AN 1998-169439 [15] corresp. to WO 93 08272.

(Continued)

*Primary Examiner*—Manjunath Rao
*Assistant Examiner*—Yong Pak
(74) *Attorney, Agent, or Firm*—Collard & Roe, P.C.

(57) ABSTRACT

A pyrF gene is useful as a selection marker gene for an expression system for the production of proteins in mushrooms of the genus *Trametes, Coriolus* or *Polyporus*. The pyrF gene includes a DNA sequence SEQ ID NO: 1 from position 1133 up to and including position 1877 or DNA-sequence SEQ, ID NO: 2 from position 1 up to and including position 684 or a DNA-sequence with a sequence homology greater than 60% relative to the above-mentioned regions of sequence SEQ ID NO: 1 or SEQ ID NO: 2.

5 Claims, 3 Drawing Sheets

OTHER PUBLICATIONS

Jef D. Boeke et al., Methods in Enzymology, 154, (1987), pp 164-174.
Gene, 53 (1987), pp 201-209. "Genbank" database, AN Kej 001358.gb_pe.
M. Sanchez et al., Yeast 11 (1995), pp. 425-433.
R. Contreras et al., Bio/Technology, 9 (1991) pp. 378-381.
Broekhuijsen et al., Journal of Biotechnology, 31 (1993), pp. 135-145.
Germann et al., Journal of Biological Chemistry, 263 (1988) pp. 885-896.
Eggert et al., Applied and Environmental Microbiology, 62 (1996), pp. 1151 to 1158.
Martinez et al., Appl. Microbiol. Biotechnol., 41 (1994), pp. 500-504.
Yaver et al., Applied and Environmental Microbiology, 62 (1996), pp. 834-841.
Velayos et al., Mol. Gen. Genet., 260 (1998) pp 251-260.
Yamagishi et al., Appl. Environ. Microbiol., 62 (1996), No. 6, pp. 2191-2194.

* cited by examiner

Primer A: 5'-TTYGGICCIGCITAYAARGGIATHCC-3'  SEQ ID NO: 4

FIG. 3

Primer B: 5'-TTICCICCYTCICCRTGRTCYTT-3'  SEQ ID NO: 5

FIG. 4

Oligo PyF-1:
5'-CTAG<u>ACATGT</u>CGCTCGAAAAATACCAGACAGAGCT-3'  SEQ ID NO: 6

FIG. 5

Oligo PyF-2:
5'-CTGTCTGGTATTTTTCGAGCG<u>ACATGT</u>CTAGAGCT-3'  SEQ ID NO: 7

FIG. 6

SEQUENCE LISTING

<160> NUMBER OF SEQ ID NOS: 7

<210> SEQ ID NO 1
<211> LENGTH: 3448
<212> TYPE: DNA
<213> ORGANISM: Trametes versicolor
<220> FEATURE:
<221> NAME/KEY: gene
<222> LOCATION: (1133)..(1877)
<223> OTHER INFORMATION:
<220> FEATURE:
<221> NAME/KEY: promoter
<222> LOCATION: (1)..(1132)
<223> OTHER INFORMATION:
<220> FEATURE:
<221> NAME/KEY: 3'UTR
<222> LOCATION: (1878)..(3448)
<223> OTHER INFORMATION:
<220> FEATURE:
<221> NAME/KEY: Intron
<222> LOCATION: (1226)..(1286)
<223> OTHER INFORMATION:

<400> SEQUENCE: 1

```
gatctcgagt aggatggaga acggtataac gatgccagag atgataggtg tccagcggta      60
gttgggaacg aggctgtcta ggtcggcgtt cttgtcgtcg gtcggccaga ggtacgattt     120
gaggcgagag tatagagata tccctaggag tgtgacgtca tcggacgagt taccctccgc     180
ggtatgttgt gtactgtcca ccttctccgg gtcagacggt tgtgatgtac tgcgtccggg     240
ttggagcgtc aggaaaagcg cagacaggct gaagagtccc attccgccgc agaaggtgtg     300
cgaggggaa agtgccagtg tagcagtgag gcgtgcctac gatatgagac ggacatggtc      360
agtatctatg cccggtcaag gtcgccgcac agacctcact gtaacctcat ggcaatgtcg     420
cggatgcaca aagcaggtag agatgttcaa atggggcacg gagcgggtcg tccggagcgc     480
tctccctcgg ctctttgcaa ggcagctggc ggatgtttgg tcagttgagg tactgcatcc     540
cttgcaatag cgaaaacagc tcaccagacg tgagtatatg ctgtatacgg gagaaggaag     600
cggaacaccg tgagtggaag agatgaagtg gttatgaata catcccggtg gaggttgagt     660
ctaacagcgt cggatctcgc tgcgttccgg agcagaggcc cggtacgagc gccggtgtct     720
gctcgtgttc cggcacgccg tatgctcgta aatcaccttt agaaaacttg aataagtgag     780
agaagatacg aaacgtcagt ctgcacctat ggagatatgt aaaaatcgca aaacatagc      840
gttgacgcta taaaaaagaa aaggacaaaa tgaccaccgc aggggtcgaa cctgcaatct     900
cctgatccct aggtttgaag gttcatcacc tcaattcgta gtcagacgcg atgccatttc     960
gccaggcggc cgttagaaac gaaactacta cgtttaaacc cgggtataac acagcctagt    1020
```

```
attccgtgcg ggccgcgccg ccgataagct tgttttcgtg aactgtcttc cccctcctgc   1080
atctcgattc tcgacctcca tcgccgcgac gatcccttcc ttcccactca ccatgtcgct   1140
cgaaaaatac cagacagagc tcatcgagca cggcatgacc gccggtgcgc tcaagttcgg   1200
gaccttcacc ctcaaatcag gccggtccgt cccctcccta ggctgcgcgc cgctctcccc   1260
gtgaacgctc cctcaccccg cgcaggacct cgccctactt cttcaacgcc ggcctgctcg   1320
cgtccgggcc cgtgctcgac acgctgtgct ccgcgtacgc cgcgacgatc gcgcgcgcgc   1380
tcaaggcgtc gcccgggctg cccgcgttcg acgtgctctt cgggcccgcg tacaagggca   1440
tcccgttcgc ggcggggacc gcgctgctgc tgcaccgcga ccacggcatc accgtcgggt   1500
tcgcgtacga ccgcaaggag gcgaaggatc atggggaggg cgggatactt gtgggcgcgc   1560
cggtgagggg caagcgcgtg ctggtgctgg acgacgtcgc gacggcgggc acggcgatcc   1620
gccaggcgat tgagactgtg acgaaggagg ggggcgaggg cgttggcgcg gtgttgatgc   1680
tcgatcggca ggaggtgggc aaggagggga agagcacgct tgcggaggtg gaggcgctgt   1740
tgggcgggaa gggacgtgtg ccgacgatcc tgaggatgaa ggacctcatg aagtggttgc   1800
aggagcacgg ccggacggag gagcttgcga agatgcaaga gtactgggag cagtacggcg   1860
cgaaggaaag cgaatgagaa gacacgaagg cagttgtgta ctaggtgagt aacaccacgc   1920
tacatcgatc catccactaa acccatgcag atgaagaccc actgtacaat ttctcggtac   1980
ctgtcacgtt gaacgcaaag agccgaagat gtgagagtac acatgccatt catcccgata   2040
tatagcacaa gaacatgtag taatagaacc tgcagaaaca caaagcatga tcagcaagac   2100
tccatgggca ctgagttatg atgaactaac cgctatcacc aaaaacaccg ctcttattcg   2160
cccaaccgac gacccgaacc ccagttatat cctcccacac cgctcgcagc agcagcagca   2220
gcagcctgct ccctgaccct ccgtgggggc acaacatgca cgcccccacc gacattcgca   2280 acgccccga ccccacccgt cgcgccccca ctagcagact ccccgaacca cccgcgcagc   2340
cacgccggcg ccgtacctgc agccctgagc gagccggtgt caaagacagt ccaccaccag   2400
aggtggccga cgacagcccc agagatgctg atggcagcgg cgccggggcc gcccatgagg   2460
aggtccatgc cgacgagcat gtaggggaagg tagatgacgg ggaaggtgat gagcccgaag   2520
aaggatgtct gggacccagg tggggcgagc cgggaggaga cgtaggtgag cgcgaggagg   2580
agcgcgcggg tgtgcacaaa ggtgccgagg ggaatgttga ggccctggtg tgaggcgggt   2640
tagcgcaaag gtcagaggcg ggatgatact attggacgta cgaggatagc aagtcctgcg   2700
agcgagagct gccatgcgta gtctgaagag cggcggggga agtgtgtctc ttctagctca   2760
ttggaatttc gactagtttc aagtgtacgg tcctcagtat catcatgtat tgcaacagtg   2820
tcatacgcac tagagcatcg caaggtcgaa gatgaagttg atccccgagc ctataaagac   2880
aaggtcagca ccgacatggc atgtagtcag acaagattga gtacgcactt cccaagaaga   2940
agctcgtaaa cactctccag atctacatta agacgtgagt atcgcatacc ttctcagtgc   3000
ctgacttatc tttcatccaa ctacagagac agaaacccac ctcaaacttc tgcgtaacga   3060
actccttcac aaagacgacc ttgtatattg gcaagatttg caggagcact ggcaaggtga   3120
cggcgagaga ggaggcgcat agaaaccgag tgactggagg gattttgcga atctcatcca   3180
tgaaagacat cttgaggaga ctggaggtga gtagagcgat agaagtacag caggcagagc   3240
agagacgacg gcagaatgtg gggaagaaca agcaggagga ggagtagagt gattttgaag   3300
taatgaaaag tggcgcaacc taatgcaaag tgtatgaggg acatccgtgg acataaagta   3360
```

-continued

```
ttccgcacct cgggcaagac attcaatctc agtaatgcac ttcactttcg gagttcaact    3420
tcaaactcga ctttgaaact tgagatcc                                        3448
```

<210> SEQ ID NO 2
<211> LENGTH: 684
<212> TYPE: DNA
<213> ORGANISM: Trametes versicolor
<220> FEATURE:
<221> NAME/KEY: CDS
<222> LOCATION: (1)..(684)
<223> OTHER INFORMATION:

<400> SEQUENCE: 2

```
atg tcg ctc gaa aaa tac cag aca gag ctc atc gag cac ggc atg acc      48
Met Ser Leu Glu Lys Tyr Gln Thr Glu Leu Ile Glu His Gly Met Thr
1               5                   10                  15 gcc ggt gcg ctc aag ttc ggg acc ttc acc ctc aaa tca ggc cgg acc      96
Ala Gly Ala Leu Lys Phe Gly Thr Phe Thr Leu Lys Ser Gly Arg Thr
            20                  25                  30 tcg ccc tac ttc ttc aac gcc ggc ctg ctc gcg tcc ggg ccc gtg ctc     144
Ser Pro Tyr Phe Phe Asn Ala Gly Leu Leu Ala Ser Gly Pro Val Leu
        35                  40                  45 gac acg ctg tgc tcc gcg tac gcc gcg acg atc gcg cgc gcg ctc aag     192
Asp Thr Leu Cys Ser Ala Tyr Ala Ala Thr Ile Ala Arg Ala Leu Lys
    50                  55                  60 gcg tcg ccc ggg ctg ccc gcg ttc gac gtg ctc ttc ggg ccc gcg tac     240
Ala Ser Pro Gly Leu Pro Ala Phe Asp Val Leu Phe Gly Pro Ala Tyr
65                  70                  75                  80 aag ggc atc ccg ttc gcg gcg ggg acc gcg ctg ctg ctg cac cgc gac     288
Lys Gly Ile Pro Phe Ala Ala Gly Thr Ala Leu Leu Leu His Arg Asp
                85                  90                  95 cac ggc atc acc gtc ggg ttc gcg tac gac cgc aag gag gcg aag gat     336
His Gly Ile Thr Val Gly Phe Ala Tyr Asp Arg Lys Glu Ala Lys Asp
            100                 105                 110 cat ggg gag ggc ggg ata ctt gtg ggc gcg ccg gtg agg ggc aag cgc     384
His Gly Glu Gly Gly Ile Leu Val Gly Ala Pro Val Arg Gly Lys Arg
        115                 120                 125 gtg ctg gtg ctg gac gac gtc gcg acg gcg ggc acg gcg atc cgc cag     432
Val Leu Val Leu Asp Asp Val Ala Thr Ala Gly Thr Ala Ile Arg Gln
    130                 135                 140 gcg att gag act gtg acg aag gag ggg ggc gag gtc gtt ggc gcg gtg     480
Ala Ile Glu Thr Val Thr Lys Glu Gly Gly Glu Val Val Gly Ala Val
145                 150                 155                 160 ttg atg ctc gat cgg cag gag gtg ggc aag gag ggg aag agc acg ctt     528
Leu Met Leu Asp Arg Gln Glu Val Gly Lys Glu Gly Lys Ser Thr Leu
                165                 170                 175 gcg gag gtg gag gcg ctg ttg ggc ggg aag gga cgt gtg ccg acg atc     576
Ala Glu Val Glu Ala Leu Leu Gly Gly Lys Gly Arg Val Pro Thr Ile
            180                 185                 190 ctg agg atg aag gac ctc atg aag tgg ttg cag gag cac ggc cgg acg     624
Leu Arg Met Lys Asp Leu Met Lys Trp Leu Gln Glu His Gly Arg Thr
        195                 200                 205 gag gag ctt gcg aag atg caa gag tac tgg gag cag tac ggc gcg aag     672
Glu Glu Leu Ala Lys Met Gln Glu Tyr Trp Glu Gln Tyr Gly Ala Lys
    210                 215                 220 gaa agc gaa tga                                                      684
Glu Ser Glu
225
```

<210> SEQ ID NO 3
<211> LENGTH: 227

```
<212> TYPE: PRT
<213> ORGANISM: Trametes versicolor

<400> SEQUENCE: 3

Met Ser Leu Glu Lys Tyr Gln Thr Glu Leu Ile Glu His Gly Met Thr
1               5                   10                  15

Ala Gly Ala Leu Lys Phe Gly Thr Phe Thr Leu Lys Ser Gly Arg Thr
            20                  25                  30

Ser Pro Tyr Phe Phe Asn Ala Gly Leu Leu Ala Ser Gly Pro Val Leu
        35                  40                  45

Asp Thr Leu Cys Ser Ala Tyr Ala Ala Thr Ile Ala Arg Ala Leu Lys
    50                  55                  60

Ala Ser Pro Gly Leu Pro Ala Phe Asp Val Leu Phe Gly Pro Ala Tyr
65                  70                  75                  80

Lys Gly Ile Pro Phe Ala Ala Gly Thr Ala Leu Leu His Arg Asp
                85                  90                  95

His Gly Ile Thr Val Gly Phe Ala Tyr Asp Arg Lys Glu Ala Lys Asp
            100                 105                 110

His Gly Glu Gly Gly Ile Leu Val Gly Ala Pro Val Arg Gly Lys Arg
            115                 120                 125

Val Leu Val Leu Asp Asp Val Ala Thr Ala Gly Thr Ala Ile Arg Gln
130                 135                 140

Ala Ile Glu Thr Val Thr Lys Glu Gly Gly Glu Val Val Gly Ala Val
145                 150                 155                 160

Leu Met Leu Asp Arg Gln Glu Val Gly Lys Glu Gly Lys Ser Thr Leu
                165                 170                 175

Ala Glu Val Glu Ala Leu Leu Gly Gly Lys Gly Arg Val Pro Thr Ile
            180                 185                 190

Leu Arg Met Lys Asp Leu Met Lys Trp Leu Gln Glu His Gly Arg Thr
                195                 200                 205

Glu Glu Leu Ala Lys Met Gln Glu Tyr Trp Glu Gln Tyr Gly Ala Lys
    210                 215                 220

Glu Ser Glu
225

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:  PrimerA
<220> FEATURE:
<221> NAME/KEY: primer_bind
<222> LOCATION: (1)..(26)
<223> OTHER INFORMATION: n = i
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (9)..(9)
<223> OTHER INFORMATION: n = i
<220> FEATURE:
<221> NAME/KEY: misc_feature
<222> LOCATION: (12)..(12)
<223> OTHER INFORMATION: n = i
<220> FEATURE:
<221> NAME/KEY: misc_feature
<222> LOCATION: (21)..(21)
<223> OTHER INFORMATION: n = i

<400> SEQUENCE: 4
```

```
ttyggnccng cntayaargg nathcc                                              26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: PrimerB
<220> FEATURE:
<221> NAME/KEY: primer_bind
<222> LOCATION: (1)..(23)
<223> OTHER INFORMATION: n = i
<220> FEATURE:
<221> NAME/KEY: misc_feature
<222> LOCATION: (3)..(3)
<223> OTHER INFORMATION: n = i
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (12)..(12)
<223> OTHER INFORMATION: n = i

<400> SEQUENCE: 5 ttncnccyt cnccrtgrtc ytt                                                  23

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: PyF-1
<220> FEATURE:
<221> NAME/KEY: misc_feature
<222> LOCATION: (1)..(35)
<223> OTHER INFORMATION:

<400> SEQUENCE: 6
ctagacatgt cgctcgaaaa ataccagaca gagct                                    35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: PyF-2
<220> FEATURE:
<221> NAME/KEY: misc_feature
<222> LOCATION: (1)..(35)
<223> OTHER INFORMATION:

<400> SEQUENCE: 7
ctgtctggta tttttcgagc gacatgtcta gagct                                    35
```

PYRF GENE AND THE UTILIZATION THEREOF

CROSS REFERENCE TO RELATED APPLICATIONS

Applicant claims priority under 35 U.S.C. §119 of German Application No. 199 34 408.6 filed Jul. 22, 1999. Applicant also claims priority under 35 U.S.C. §120 of PCT/EP00/06091 filed Jun. 29, 2000. The international application under PCT article 21(2) was not published in English.

BACKGROUND OF THE INVENTION

1. Field of the Invention

The invention relates to a pyrF gene and its use as selection marker gene for an expression system for producing proteins in fungi of the genera *Trametes, Coriolus* or *Polyporus*.

2. The Prior Art

Various prokaryotic and eukaryotic expression systems are known for producing proteins. The application DE-A-19814853 describes in detail the prior art in this regard. DE-A-19814853 itself discloses a process for transforming filamentous fungi from the genera *Trametes* and *Polyporus*, with which it is possible to achieve significantly higher production rates for a protein expressed in each case. The application discloses expression vectors which comprise genetic regulatory elements for expression in filamentous fungi of the class Basidiomycetes. On transformation of filamentous fungi of the class Basidiomycetes they permit positive transformants to be selected on the basis of the complementation of an auxotrophic gene defect.

The gene defect disclosed in DE-A-19814853 relates to the pyrG gene. This gene codes for orotidine-5'-phosphate decarboxylase. DE-A-19814853 also discloses strains with a defect in the pyrg gene which are able to grow on minimal medium only in the presence of uridine (uridine auxotrophy). After transformation of these strains with DNA vectors which comprise an intact pyrG gene, the uridine-auxotrophic strains again grow on minimal medium without uridine (uridine prototrophy).

Uridine-auxotrophic strains are isolated in the state of the art (Boeke et al., Methods Enzymol. (1987) 154, 164–175) by treatment with the genotoxic substance 5-fluoroorotic acid (FOA). Uridine-auxotrophic strains generated on treatment with FOA have a genetic defect either in the pyrG gene or in the pyrF gene. The pyrF gene is also called the ura5 gene. It codes for the enzyme orotate phosphoribosyltransferase.

Uridine-auxotrophic Basidiomycetes strains with a defect in the pyrF gene would also be valuable strains for transformation with the aim of producing proteins if the intact pyrF gene from Basidiomycetes were available as selection marker gene for efficient transformation. However, pyrF genes have to date been described only for fungi from the class Ascomycetes such as, for example, Podospora anserina (Gene 53 (1987), 201–209), *Kluyveromyces lactis* (unpublished, the DNA sequence is deposited in the "Genbank" database under the accession number klj001358.gb_pl) or *Yarrowia lipolytica* (M. Sanchez et al., Yeast 11 (1995), 425–433). On the other hand, no pyrF genes from filamentous fungi from the class Basidiomycetes such as, for example, of the genera *Trametes, Coriolus* or *Polyporus* are known.

SUMMARY OF THE INVENTION

One object of the present invention is to provide pyrF genes from filamentous fungi from the class Basidiomycetes. These genes are suitable for use as selection marker genes for the transformation of uridine-auxotrophic strains.

The present invention relates to a DNA sequence which codes for a protein having the enzymatic activity of orotate phosphoribosyltransferase (pyrF activity), which comprises the chromosomal DNA sequence SEQ ID NO: 1 from position 1133 up to and including position 1877, or comprises the cDNA sequence SEQ ID NO: 2 from position 1 up to and including position 684, or comprises a DNA sequence having a sequence homology of more than 60% with the DNA sequence SEQ ID NO: 1 or SEQ ID NO: 2.

A preferred DNA sequence has a sequence homology of more than 70% with the DNA sequence SEQ ID NO: 2.

In a particularly preferred embodiment, the present invention comprises a DNA sequence having a sequence homology of more than 80% with the DNA sequence SEQ ID NO: 2.

All the values mentioned for the homology in the present invention relate to results obtained with the computer program "Wisconsin Package Version 9.1, Genetics Computer Group (GCG), Madison, Wis.". The homology is determined by searching the database with the subprogram "blast" and the preset values (hit frequency 10.0). The sequences with the greatest similarity are then examined for homology using the subprogram "gap". The preset parameters "gap creation penalty 50" and "gap extension penalty 3" are used in this in order to compare DNA sequences. The preset parameters "gap weight 8" and "length weight 2" are used to compare amino acid sequences.

The DNA sequence of the invention SEQ ID NO: 1 from position 1133 up to and including position 1225 and from position 1287 up to and including position 1877, and the cDNA sequence derived therefrom SEQ ID NO: 2 from position 1 up to and including position 684 codes for a protein having pyrF activity.

The present invention therefore also relates to a protein having pyrF activity, which comprises the amino acid sequence SEQ ID NO: 3 or comprises an amino acid sequence having a sequence homology of more than 60% with amino acid sequence SEQ ID NO: 3.

The preferred amino acid sequence has a sequence homology of more than 70% with the amino acid sequence SEQ ID NO: 3.

A particularly preferred amino acid sequence in the present invention is one with a sequence homology of more than 80% with the amino acid sequence SEQ ID NO: 3.

The DNA sequence SEQ ID NO: 1 from position 1226 up to and including position 1286 is an intron which is not translated into amino acid sequence.

The DNA sequence SEQ ID NO: 1 represents from position 1 to position 1132 the DNA sequence for the promoter region for transcription of the pyrF gene from *Trametes versicolor*. This promoter sequence can be replaced by any other promoter sequences for the transcription.

The DNA sequence of the invention can be obtained, for example, by cloning from the Basidiomycetes strain *Trametes versicolor* TV-1 (deposited at the DSMZ Deutsche Sammlung von Mikroorganismen und Zellkulturen GmbH, D-38124 Braunschweig under the number DSM 11523). For this purpose, a *Trametes versicolor* TV-1 gene library is constructed by methods known per se. This may be a cDNA or a genomic gene library.

The DNA sequence of the invention is isolated from the gene library by using DNA probes which contain pyrF-specific DNA sequences. Such DNA probes can be obtained, for example, by a PCR reaction using DNA primers from genomic DNA of *Trametes versicolor* TV-1.

The primers used are degenerate DNA sections with a length of, preferably, 23 to 26 bp, whose sequence is established by comparison with sequences of known pyrF genes. The DNA sections suitable as primers are preferably obtained by oligonucleotide synthesis of the established DNA sections. A pyrF gene of the invention can be isolated, for example, as described in examples 1 to 3.

A pyrF gene which has been isolated in this way, for example, can be modified at any desired position in the sequence by techniques known to the skilled worker, such as, for example, site directed mutagenesis. The invention therefore also comprises a DNA sequence coding for a protein having pyrF activity comprising a DNA sequence with a sequence homology of more than 60%, preferably 70%, particularly preferably 80%, with the DNA sequence SEQ ID NO: 2 from position 1 up to and including position 684.

To express the DNA of the invention, the latter is cloned in an expression vector in a manner known per se, and this expression vector containing the pyrF gene is introduced into a microorganism and expressed in the microorganism.

The invention therefore also relates to an expression vector which comprises a pyrF gene of the invention.

The expression vectors of the invention are particularly suitable for expressing genes which code for proteins in a host organism of the genus *Trametes, Coriolus* and *Polyporus*. Genes which code for proteins mean for the purpose of the invention also the cDNA genes derived from the structural genes of the proteins. The proteins may be proteins which are heterologous for the host organism or proteins which are homologous for the host organism.

The expression vector of the invention thus preferably also comprises at least one gene which codes for a protein to be expressed.

The expression vector of the invention particularly preferably comprises at least one gene which codes for a hydrolytic enzyme, for example from the group of cellulases, hemicellulases and lipases or from the group of oxidoreductases such as, for example, the lignin peroxidases, manganese peroxidases, laccases, cellobiose-quinone oxidoreductase or cellobiose oxidase.

The expression vector of the invention particularly preferably comprises a gene for a laccase.

The expression vector of the invention may be a DNA construct which is integrated into the genome of the host organism and replicated together with the latter. Alternatively, the expression vector may be an autonomously replicating DNA construct which is not integrated into the host genome, such as, for example, a plasmid, an artificial chromosome or a comparable extrachromosomal genetic element.

An expression vector of the invention ought preferably also to comprise the following genetic elements:

a promoter which mediates the expression of a protein-encoding gene in the host organism. This ought preferably to be a strong promoter, so that high expression efficiency can be ensured. The promoter is preferably functionally linked to the 5' end of the gene to be expressed. The promoter may originate from the gene to be expressed, or else the promoter of a foreign gene can be used.

Suitable and preferred promoters are selected from the group of promoters active in filamentous fungi of the class Basidiomycetes, such as, for example, the GAPDH promoter from *Trametes versicolor*, promoters for laccase genes from *Trametes versicolor* or *Polyporus* pinsitus, the promoter for the Ornithine trans-carbamoylase gene or the GAPDH gene from *Coriolus hirsutus* or the GAPDH promoter from *Agaricus bisporus*.

The GAPDH promoter from *Trametes versicolor* is particularly preferred. This promoter is disclosed in DE-A-19814853, example 5, and DE-A-19814853, SEQ ID NO: 3, base 1–1542.

The expression vector ought also preferably to comprise signals suitable for the host organism for termination of transcription and, in eukaryotes, additional signals for polyadenylation, which signals are functionally linked to the 3' end of the gene to be expressed. Such signals for termination of transcription and polyadenylation are shown, for example, in SEQ ID NO: 1, bp 1878–3448.

The transcription terminator used can be the terminator of the protein-encoding gene to be expressed or else the terminator of a foreign gene. The transcription terminator from a laccase gene is preferably used.

Expression of the proteins can take place intra-cellularly or, in the presence of a signal sequence capable of functioning for the purpose of secretion, also extracellularly.

If secretion of the expressed protein from the cell is desired, the expression vector of the invention preferably comprises a signal sequence capable of functioning 5' upstream of the protein-encoding gene. It is additionally possible for a so-called secretion carrier, functionally linked to the 5' end of the protein-encoding gene, to be present in the expression vector of the invention.

The secretion carrier may be the gene for a secreted protein or the fragment of a gene for a secreted protein. The secretion carrier can be functionally linked to the protein to be secreted in such a way that a fusion protein is produced from the secretion carrier and the protein to be secreted. In another embodiment, the linkage of secretion carrier and the protein to be secreted is designed so that the secretion carrier can be separated from the protein to be secreted. This can be brought about, for example, by inserting a recognition sequence for a protein-cleaving enzyme into the linkage site between the secretion carrier and the protein to be secreted. An example of this which may be mentioned is the lysine-arginine recognition sequence for the so-called KEX2 protease and an example of a secretion carrier is the glucoamylase from *Aspergillus niger* (Contreras et al., Bio/Technology (1991) 9, 378–381, Broekhuijsen et al., J. of Biotechnology (1993) 31, 135–145).

DNA sequences which are involved other than as transcription terminators at the 3' end of the protein-encoded gene in the expression and secretion of the expressed gene can likewise be present in the DNA vector of the invention. One example thereof is provided by the gene for the laccase from *Neurospora crassa*, whose 3' end contains the sequence for 13 amino acids which are deleted during secretion of the protein and are no longer present in the mature protein (Germann et al., J. Biol. Chem. (1988) 263, 885–896).

Preparation of the expression vectors of the invention takes place by methods known in the prior art. Various possibilities are explained in the examples. The methods described therein can be applied by the skilled worker to any desired other vectors, resistance genes, regulatory elements and structural genes.

The invention further relates to microorganisms which comprise an expression vector of the invention.

Microorganisms suitable for the expression of an expression vector of the invention are strains of filamentous fungi from the class Basidiomycetes.

Strains from the genera *Trametes, Coriolus* and *Polyporus* are particularly suitable.

Particularly preferred host organisms are monokaryotic strains from the genera *Trametes, Coriolus* and *Polyporus*.

Host organisms of the species *Trametes versicolor* are particularly preferred.

The host organism is preferably distinguished by having a genetic defect in metabolism (auxotrophy), on the basis of which the essential metabolite uridine can no longer be synthesized, and the host organism is no longer able to grow on minimal medium without addition of this metabolite.

The expression vectors of the invention permit the selection of positive transformants on the basis of complementation of an auxotrophic gene defect in the host organism on transformation of fungi selected from the genera *Trametes, Coriolus* and *Polyporus*.

The expression vectors of the invention are suitable for producing fungal strains which are capable of efficient expression and secretion of proteins.

The invention therefore also relates to processes for the production of fungal strains which are capable of efficient expression and secretion of proteins.

This process, in which a fungus with an auxotrophic gene defect is transformed as host strain in a transformation mixture, using process steps known per se, with an expression vector which has a gene for complementation of the auxotrophic gene defect in the host strain, and clones transformed with the expression vector are selected from the transformation mixture by selection for complementation of the auxotrophic gene defect, where expression of the gene for complementation of the auxotrophic gene defect in the host strain is controlled by a genetic regulatory element which is active in the host strain, comprises employing as host strain a uridine-auxotrophic fungus selected from the genera *Trametes, Coriolus* and *Polyporus* with a gene defect in the pyrF gene.

The preferred host for gene expression is a monokaryotic basidiomycete from the genus *Trametes, Coriolus* or *Polyporus*.

A host particularly preferred for gene expression is of the species *Trametes versicolor* having a defect in the pyrF gene and being auxotrophic for uridine.

The invention also relates to an expression system comprising a host strain selected from the genera *Trametes, Coriolus* and *Polyporus* having a genetic defect in metabolism, on the basis of which the metabolite uridine which is essential for growth is no longer synthesized, and the host strain is no longer able to grow on minimal media without addition of this metabolite, and to an expression vector comprising a selection marker gene which complements the auxotrophic gene defect of the host strain, wherein the host strain has as genetic defect in metabolism a defect in the pyrF gene, and the selection marker gene is a pyrF gene.

The pyrF gene is preferably derived from a fungus of the genus *Agaricus, Coriolus, Polyporus, Pleurotus, Phanerochaete, Schizophyllum* or *Trametes*.

Particularly suitable as selection marker gene for the expression system of the invention is the orotate phosphoribosyltransferase gene (pyrF gene) from a filamentous fungus of the class Basidiomycetes *Trametes versicolor*.

The expression vectors of the invention are particularly suitable for expressing the pyrF gene.

Expression of the pyrF gene from the basidiomycete *Trametes versicolor* is preferably regulated by the promoter and, where appropriate, terminator for the pyrF gene from *Trametes versicolor*.

The expression system of the invention is particularly suitable for expressing a gene which codes for a hydrolytic enzyme, for example from the group of proteases, cellulases, hemicellulases and lipases or from the group of oxidoreductases such as, for example, the lignin peroxidases, manganese peroxidases, laccases, cellobiose-quinone oxidoreductase or cellobiose oxidase.

It is particularly suitable and preferred for expressing a gene for a laccase.

Transformation of the host strain takes place by methods corresponding to the prior art. These methods include transformation of protoplasts by the $CaCl_2$/PEG method, transformation by electroporation or biolistic transformation by bombardment with DNA-containing microprojectiles. These methods are described in standard text books.

For example, the gene to be transformed is cloned in a know manner into an expression vector of the invention and introduced by the methods mentioned into a filamentous fungus selected from the genera *Trametes, Coriolus* and *Polyporus*.

The gene to be transformed may, however, also be cloned into an expression vector without a selection marker gene and be used together with the vector which complements the auxotrophic gene defect in the host strain for generating transformants (cotransformation).

The strain to be used for the transformation is a uridine-auxotrophic filamentous fungus selected from the genera *Trametes, Coriolus* and *Polyporus*. The relevant strain from the class Basidiomycetes may be a monokaryotic or else a dikaryotic strain. In a preferred embodiment, it is a uridine-auxotrophic strain which has a defect in the pyrF gene.

Particularly preferred for the transformation is a monokaryotic, uridine-auxotrophic, pyrF-deficient strain from the species *Trametes versicolor*.

The selection of positive transformants takes place, for example, by placing protoplasts, after transformation with vector DNA, on a medium to which is added, for osmotic stabilization of the protoplasts, an addition such as, for example, sorbitol, mannitol or sucrose and which allows the selection of transformants with the complementing pyrF gene.

In a preferred embodiment of the invention, the filamentous fungus *Trametes versicolor* is transformed in a homologous system with the gene of a laccase from *Trametes versicolor*. This achieves an increase in the expression rate for said laccase, which significantly improves the production rate in the fermentation of 0.1 g of laccase/l of culture medium which can be achieved in the prior art.

Preferably used for this purpose is the promoter which is intrinsic to the laccase gene or the promoter for a strongly expressed gene from *Trametes versicolor*. The promoters of the laccase genes I and III, whose isolation and use is described in DE-A-19814853, are preferably used. The promoter of another strongly expressed gene is represented by the GAPDH promoter for the glyceraldehyde-3-phosphate dehydrogenase from *Trametes versicolor*.

Selection media preferably used are those on which only *Trametes versicolor* transformants which have been transformed with a functionally expressed selection marker gene for the pyrF gene are able to grow. Preference is given to the minimal medium described in the 6th example in the absence of uridine, on which pyrF-auxotrophic strains of *Trametes versicolor* are no longer able to grow or are able to grow again only after addition of uridine.

Successful use of an expression vector of the invention comprising the pyrF gene as selection system depends on efficient expression of the selection marker gene in *Trametes* transformants. Appropriate expression signals are necessary for efficient expression.

Expression signals from Basidiomycetes bring about functional expression in *Trametes versicolor* with, surprisingly, considerably greater efficiency than the expression signals otherwise available from Ascomycetes. For this reason, the pyrF selection marker gene in the DNA vectors of the invention is preferably under the control of genetic regulatory elements from Basidiomycetes, particularly preferably from those selected from the genera *Trametes, Coriolus* and *Polyporus*.

The pyrF gene is preferably under the control of the 5' promoter region upstream of it, and the 3' terminator region downstream of it. A DNA fragment in which the pyrF gene from *Trametes versicolor* is under the control of the expression signals of the pyrF gene from *Trametes versicolor* is described in SEQ ID NO: 1.

The pyrF gene may also be under the control of expression signals from Basidiomycetes which differ from those of the pyrF gene. Expression signals which comply with this function include GAPDH promoters of filamentous fungi from the class Basidiomycetes such as, for example, *Coriolus hirsutus, Phanerochaete chrysosporium, Agaricus bisporus* or *Trametes versicolor*, the OCT promoter from *Coriolus hirsutus*, the promoter of laccase I or of laccase III from *Trametes versicolor* and the terminator of the GAPDH gene from *Agaricus bisporus* or the terminators of the laccase I or laccase III gene from *Trametes versicolor*.

A particularly preferred vector is one in which the pyrF gene from *Trametes versicolor* is under the control of the expression signals of the GAPDH gene from *Trametes versicolor*. Such a vector is described in the 4th example.

A particularly preferred vector is one in which the pyrF gene from *Trametes versicolor* is under the control of the expression signals of the pyrF gene from *Trametes versicolor*. Such a vector is described in the 3rd example.

The pyrF gene can be any gene which codes for a protein having the enzymatic activity of an orotate phosphoribosyltransferase.

The pyrF gene is preferably derived from a filamentous fungus from the class Basidiomycetes such as, for example, *Agaricus bisporus, Phanerochaete chrysosporium, Coriolus hirsutus, Polyporus pinsitus, Schizophyllum commune* or *Trametes versicolor*.

The pyrF gene from *Trametes versicolor* is particularly preferred.

The invention also relates to a process for producing a protein which comprises employing the expression system of the invention comprising a gene encoding the protein in a manner known per se for protein production, or comprises cultivating in a manner known per se a fungal strain which comprises a gene encoding the protein and which has been produced by the process of the invention.

Such production processes are known in principle, for example from Eggert et al., Appl. Environ. Microbiol (1996) 62, 1151–1158, Martinez et al., Appl. Microbiol. Biotechnol. (1994) 41, 500–504, or WO 93/08272.

BRIEF DESCRIPTION OF THE DRAWINGS

FIG. 3 shows the SEQ ID NO: 4 for Primer A;
FIG. 4 shows the SEQ ID NO: 5 for Primer B;
FIG. 5 shows the SEQ ID NO: 6 for Oligo PyF-1;
and
FIG. 6 shows the SEQ ID NO: 7 for Oligo PyF-2.

DETAILED DESCRIPTION OF PREFERRED EMBODIMENTS

Figure 1:
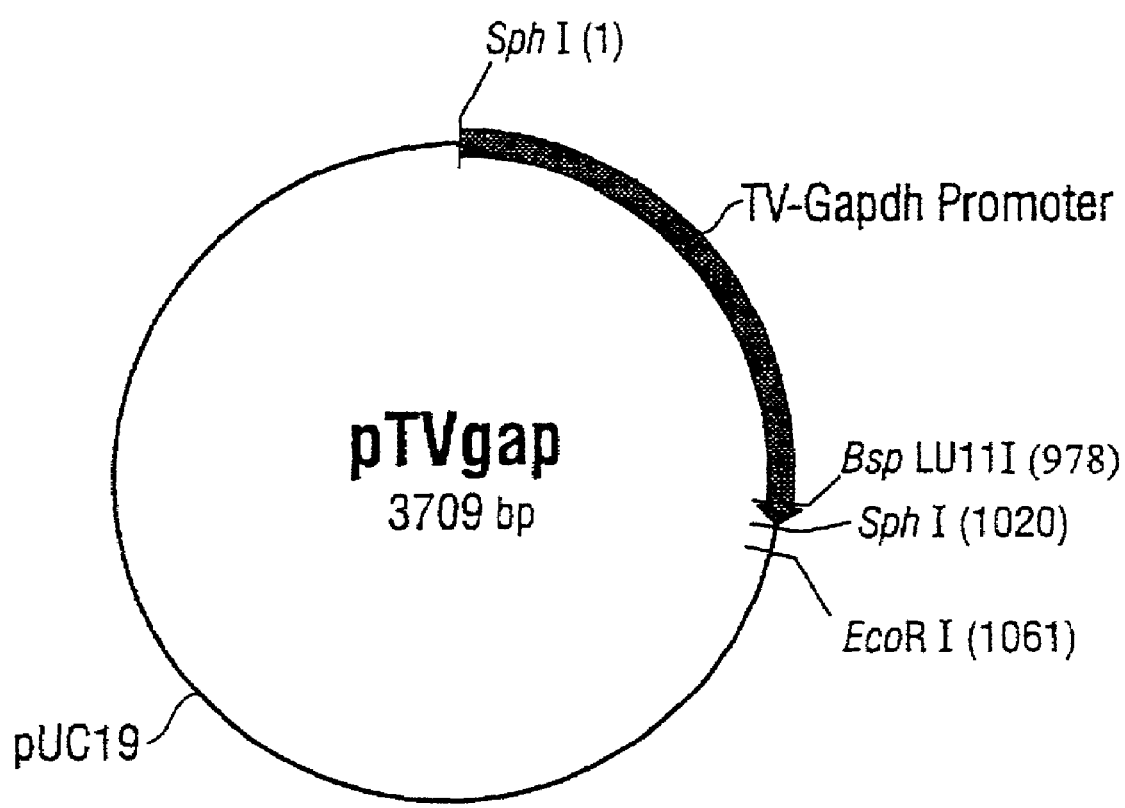
FIG. 1 shows the vector pTV gap being 3.7 kb in size.

The following examples serve to illustrate the invention further. The standard methods used in the examples for treating DNA or RNA, such as treatment with restriction endonucleases, DNA polymerases, reverse transcriptase etc., and the standard methods such as transformation of bacteria, Southern and Northern analysis, DNA sequencing, radiolabeling, screening and PCR technology were, unless indicated otherwise, carried out as recommended by the manufacturer or, if no manufacturer's instructions were available, in accordance with the prior art known from standard textbooks.

1ST EXAMPLE

Isolation of a pyrF-Specific DNA Probe

A DNA probe for isolating a pyrF gene was generated by PCR amplification from *T. versicolor* genomic DNA with degenerate primers. The degenerate primers were constructed on the basis of a comparison with sequences of known pyrF genes. Genes for orotate phosphoribosyltransferase (referred to as pyrF genes or, in another nomenclature, referred to as ura5 genes) were sought in the following gene databases: a) swissprot, b) sptrembl, c) pir, d) embl, e) genbank, f) em_tags, g) gb_tagsEMBL. Ura5, or pyrF, genes of the following organisms were selected for the sequence comparison: *Yarrowia lipolytica, Saccharomyces cerevisiae, Escherichia coli, Rhizomucor circinelloides, Colletotrichum graminicola, Trichoderma reesei* and *Sordaria macrospora*. The amino acid sequences of said pyrF genes were compared. It was possible by the comparison of sequences to identify three peptides with a length of from 6 to 9 amino acids which were completely conserved in all pyrF proteins. Two of these peptides were back-translated into DNA, taking account of degenerate codons, in order to produce degenerate primers. The primers had the following sequences (the abbreviation I refers to the base inosine):

Primer A: (See FIG. 3) SEQ ID NO: 4
Primer B: (See FIG. 4) SEQ ID NO: 5

PCR amplifications were carried out in accordance with the prior art as stated by the manufacturer (PCR kit from Qiagen, Hilden): a 50 µl PCR reaction contained 100 ng of chromosomal *T. versicolor* DNA (isolated as described in the 2nd example), the buffer provided by the manufacturer and, in addition, 1.25 U of Taq polymerase, 1.25 mM $MgCl_2$, 0.2 mM of each of the four dNTPs (DATP, dCTP, cGTP, dTTP) and in each case 100 pmol of primers A and B. The other conditions for the specific amplification of the desired PCR product were: 4 min at 94° C., followed by 10 cycles of 1 min at 94° C., 1 min at 45° C. and 1 min at 65° C., and 30 cycles of 1 min at 94° C., 1 min at 50° C. and 1 min at 72° C. A PCR product of about 140 bp was obtained. The PCR product was purified by agarose gel electrophoresis, cloned into the pCR-Script vector (cloning kit from Stratagene, Heidelberg) and transformed into *E. coli*. The plasmid was isolated from cultivation of transformed E. coli. A DNA sequence analysis from the 5' and 3' ends confirmed that the cloned DNA fragment was the fragment of a pyrF gene.

To prepare the DNA probe for screening pyrF genes, the pyrF-specific PCR fragment was cut out by treatment with Not I and Eco RI, isolated by agarose electrophoresis and labeled with the nonradioactive "Gene Images" detection kit from Amersham, Braunschweig.

2ND EXAMPLE

Production of a Chromosomal Gene Library from Trametes versicolor

The strain Trametes versicolor TV-1 (deposited at the DSMZ Deutsche Sammlung von Mikroorganismen und Zellkulturen GmbH, D-38124 Braunschweig under the number DSM 11523) was used. Mycelium from Trametes versicolor was firstly obtained by cultivation on malt-agar plates (3% malt extract, 0.3% peptone from soybean meal, 1.5% agar—agar, pH 5.0) at 28° C. for 7 days. Three pieces were cut out of the malt-agar plates and used to inoculate 100 ml of sterile malt extract medium (3% malt extract, 0.3% peptone from soybean meal, pH 5.0) in 500 ml Erlenmeyer flasks. The culture was incubated at 28° C. with shaking at 100 rpm for 7 days. The mycelium suspension produced in this way was filtered with suction through a porcelain funnel and washed with 0.9% saline. 1 g of mycelium from T. versicolor was ground to a fine powder with a mortar and pestle in the presence of liquid nitrogen. The powder was put into a sterile sample vessel and immediately mixed with 5 ml of extraction solution (0.1M Tris-HCl, pH 8.0, 0.1M EDTA, 0.25M NaCl, 0.6 mg/ml proteinase K) and 0.5 ml of a 10% (w/v) sodium lauroylsarcosine solution. After incubation at 50° C. for at least 2 h, the mixture was mixed with 0.85 ml of 5M NaCl and 0.7 ml of a 10% (w/v) CTAB solution in 0.7M NaCl and incubated at 65° C. for 30 min. After addition of 7 ml of a chloroform/isoamyl alcohol mixture (24:1), the mixture was shaken, the two phases were separated by centrifugation, the aqueous phase was removed, and chromosomal DNA was precipitated by adding 0.6 parts by volume of isopropanol. Further purification of the precipitated DNA took place subsequently on a column (Qiagen Genomic Tip). It was possible in this way to isolate 0.5 mg of chromosomal DNA from 16 g of mycelium.

To produce the chromosomal gene library, 90 µg of chromosomal DNA from Trametes versicolor TV-1 were cut with Sau 3A in a partial digestion and fractionated by agarose gel electrophoresis. The chromosomal DNA fragments were isolated in the range of sizes of 5–20 kb and greater than 20 kb and in each case cloned into lambda phages which had previously been cut with Bam HI ("Lambda Zap® Express" cloning system from Stratagene). $4 \times 10^4$ phages/µg of vector DNA were obtained from the 5–20 kb DNA fraction, and $5 \times 10^4$ phages/µg of vector DNA were obtained from the DNA fraction greater than 20 kb. The phages were amplified by infecting the E. coli strain XL-1 Blue MRF'.

3RD EXAMPLE

Isolation of the pyrF Gene

The chromosomal gene library from Trametes versicolor TV-1 described in the 2nd example was used. Screening for the genomic pyrF gene was carried out in accordance with the prior art. In a first round of screening, cells of E. coli XL-1 Blue MRF' were initially cultivated on 10 Petri dishes and then infected with 50 000 phages of the chromosomal gene library (5–20 kb fraction, see 2nd example) per Petri dish. After incubation at 37° C., overnight, the newly formed phages were transferred to nylon filters (Stratagene). The filters were then hybridized in accordance with the manufacturer's recommendations with the nonradiolabeled pyrF-specific probe (see 1st example). The hybridization temperature was 60° C. Positive clones were picked and purified by repeating the screening method. After three rounds of isolation, the strongly hybridizing phage clones were isolated in the screening and were recloned into the pBK CMV vector (Stratagene) by "in vivo excision" in accordance with the manufacturer's protocol (Stratagene). Analysis of the clones by digestion with restriction endonucleases and PCR showed that all the clones comprised pyrF genes. After analysis of the sequences of three clones, about 3.4 kb of sequence information was found from the longest of the pyrF clones. This pyrF clone was called pyrF61 (SEQ ID NO: 1). The pyrF61 clone contained sequence information for the pyrF structural gene (coding region, SEQ ID NO: 1, bp, 1133–1877). The coding sequence region additionally contained an intron (SEQ ID NO: 1, bp 1226–1286) which is not translated into amino acid sequence. The corresponding pyrF cDNA gene is indicated in SEQ ID NO: 2. The pyrF structural gene present in the pyrF61 clone, without the intron sequence, codes for a protein having the amino acid sequence indicated in SEQ ID NO: 3.

In addition, the pyrF61 clone also contained sequence information in the region 5' upstream of the ATG start codon (promoter region, SEQ ID NO: 1, bp 1–1132) and sequence information in the region 3' downstream of the stop codon (terminator region, SEQ ID NO: 1, bp 1878–3448). These are novel genetic regulatory elements for Trametes versicolor which can be used for producing expression vectors for gene expression in filamentous fungi from the class Basidiomycetes.

4TH EXAMPLE

Functional Linkage of the Trametes versicolor GAPDH Promoter to the pyrF Gene from Trametes versicolor A: Cloning of the pyrF Gene Into the pBluescript Vector For further processing, the pyrF gene from pyrF61 was recloned into the pBluescript vector. For this purpose, the pyrF gene was isolated as 1.6 kb Sac I-Spe I fragment from the pyrF61 clone obtained in the 3rd example and was subcloned into the pBluescript vector which had previously been cut with Sac I and Spe I. The 4.6 kb plasmid resulting therefrom was called pPyrF1.

B: Incorporation of a Linker into ppyrF1 for Functional Linkage of the ATG Translation Start Codon of the pyrF Gene to the GAPDH Promoter The pPyrF1 vector was cut with Sac I, and the linearized vector 4.6 kb in size was isolated by agarose gel electrophoresis and dephosphorylated by treatment with alkaline phosphatase. The vector prepared in this way was ligated to the linker Oligo PyF-1 (See FIG. 5) SEQ ID NO: 6
Oligo PyF-2 (See FIG. 6) SEQ ID NO: 7—.

The cleavage site for the restriction endonuclease BspLU11 I, which can be used for functional linkage to the GAPDH promoter from T. versicolor, is underlined in PyF-1 and PyF-2.

Ligation mixtures of Sac I-cut pPyrF1 with the linker oligos PyF-1 and PyF-2 were transformed into *E. coli* Top 10F' cells. Positive clones contained a newly introduced BspLU11 I cleavage site (in addition to two previously present in pPyrF1). The correct orientation of the incorporated linker, with which a BspLU11 I cleavage site had been introduced at the start ATG codon of the pyrF gene, was determined by DNA sequence analysis. The vector produced in this way (about 4.5 kb in size) was called pPyrF2.

C: Incorporation of the *T. versicolor* GAPDH Promoter into the pUC19 Vector

The DNA sequence of the promoter for the *T. versicolor* GAPDH gene is disclosed in DE-A-19814853, SEQ ID NO: 3, bp 1–1542. A promoter fragment about 1 kb in size of the GAPDH gene was isolated as Sph I fragment and cloned into a pUC19 vector. Analysis by double digestion with the restriction endonucleases Eco RI (present in the polylinker of pUC19) and BspLU11 I (present in the GAPDH promoter fragment) was followed by selection of a clone in which the BspLU11 I cleavage site was adjacent to the Eco RI cleavage site. The vector 3.7 kb in size produced in this way was called pTVgap (FIG. 1).

A unique BspLU11 I cleavage site, which would have interfered with the subsequent vector construction, had previously been deleted from the pUC19 vector used to produce pTVgap. This took place by cutting the pUC19 vector with BspLU11 I and treating the vector, which had been linearized in this way, with Klenow DNA polymerase. The ends of the pUC19 vector, which were offset after the BspLU11 I digestion, were filled in thereby. Subsequent ligation and transformation of *E. coli* Top 10F' afforded clones which contained a modified pUC19 vector without BspLU11 I cleavage site.

D: Functional Linkage of the GAPDH Promoter to the pyrF Gene

The vector pTVgap was cut with BspLU11 I and Eco RI, and the vector fragment 3.7 kb in size resulting therefrom was isolated by agarose gel electrophoresis and dephosphorylated by treatment with alkaline phosphatase.

The pyrF gene was isolated as BspLU11 I-Eco RI fragment 1.6 kb in size from the pPyrF2 vector. For this purpose, pPyrF2 was first partially cut with BspLU11 I and the linearized vector fragment 4.6 kb in size was isolated by agarose gel electrophoresis. The isolated 4.6 kb fragment was then cut with Eco RI. This resulted in the desired 1.6 kb pyrF gene fragment, which was isolated by agarose gel electrophoresis.

Figure 2:
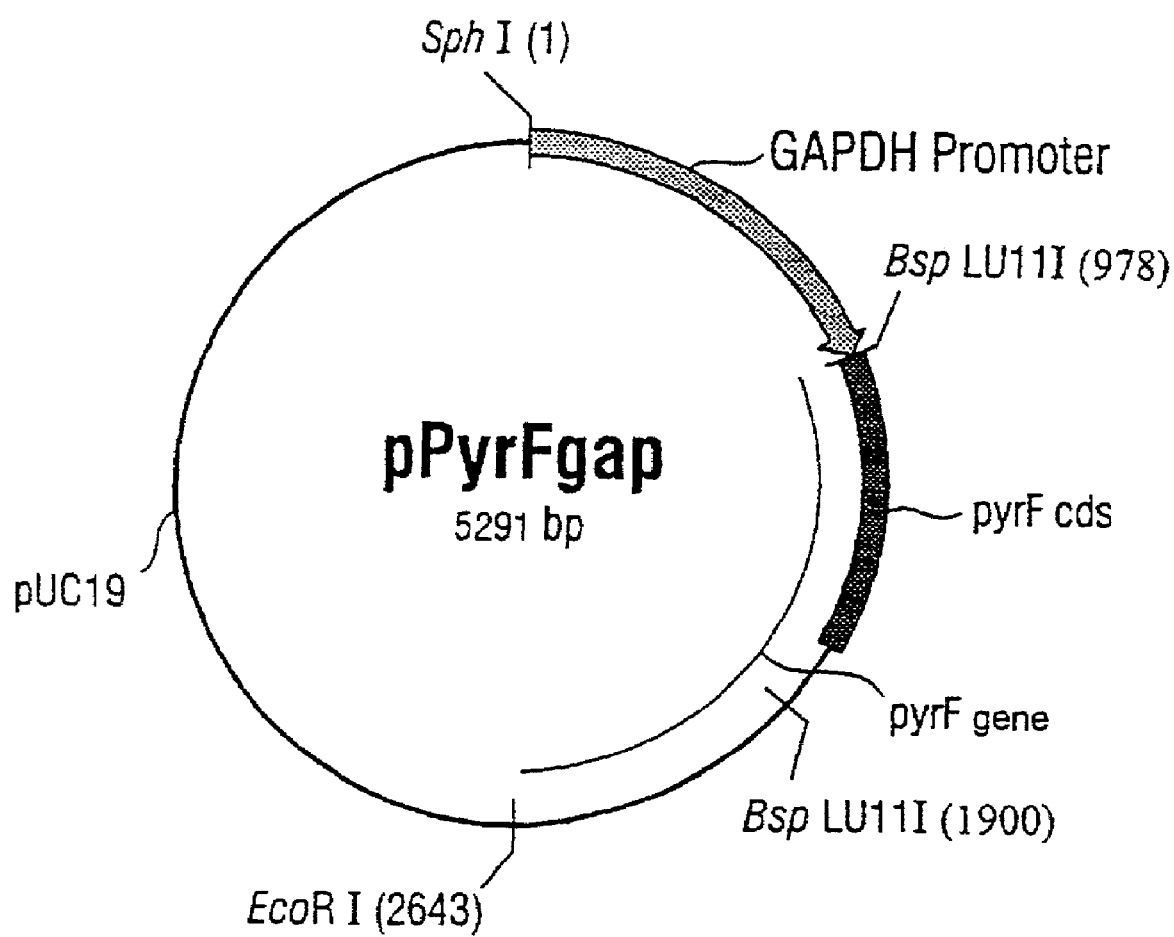
FIG. 2 shows the clone pPyr Fgap being 5.3 kb in size.

The BspLU11 I-Eco RI vector fragment 3.7 kb in size from pTVgap and the BspLU11 I-Eco RI fragment 1.6 kb in size from pPyrF2 were ligated, and *E. coli* Top 10F' cells were transformed with the ligation mixture. Clones in which the pyrF gene had been functionally linked via the BspLU11 I cleavage site to the GAPDH promoter were identified by restriction analysis. Correct linkage of the GAPDH promoter to the start ATG codon of the pyrF gene was confirmed by DNA sequencing. The correct clone had a size of 5.3 kb and was called pPyrFgap (FIG. 2).

5TH EXAMPLE

Production of *Trametes* Protoplasts and Regeneration of Fungal Colonies

The dikaryotic strains *Trametes* versicolor TV-1, *Trametes versicolor* 38070 (obtainable from the American Type Culture Collection, Rockville, Md. 20852 USA) and the monokaryotic strain *Trametes versicolor* F2 100 (deposited at the DSMZ Deutsche Sammlung von Mikroorganismen und Zellkulturen GmbH, D-38124 Braunschweig under the number DSM 11972) were used to obtain protoplasts. Mycelium from *Trametes versicolor* was first obtained by cultivation on malt-agar plates (3% malt extract, 0.3% peptone from soybean meal, 1.5% agar—agar, pH 5.0) at 28° C. for 7 days. Three pieces were cut out of the malt-agar plates and used to inoculate 100 ml of sterile malt extract medium (3% malt extract, 0.3% peptone from soybean meal, pH 5.0) in 500 ml Erlenmeyer flasks, or 125 ml of the sterile medium in 162 $cm^2$ cell culture vessels. The culture was incubated at 28° C. without shaking for 7 days until a tight mat of mycelium had grown in the culture liquid. The culture liquid was decanted off and fresh medium was added (30 ml for the mycelium in a 100 ml culture). The mycelium was homogenized with an Ultra Turrax (9 500 rpm, 4 min) and incubated at 28° C. while shaking at 100 rpm for a further 18 h.

The mycelial suspension produced in this way was harvested by centrifugation at 1 500 rpm (2 000×g) for 5 min and the mycelium obtained in this way was washed three times by suspending in 0.1M $MgSO_4$, 0.6M sucrose, 0.1M phosphate, pH 5.8 (OMT medium) and subsequently centrifuging. The isolated mycelium was weighed and stored at 4° C. until treated with lytic enzyme.

Protoplasts were produced in the following way: mycelium from a flask was suspended in 15 ml of a freshly prepared and sterile-filtered solution of the lytic enzyme mixture Novozym 234 (3 mg/ml, Novo Nordisk, Bagsvaerd, Denmark) in OMT medium in a sterile Erlenmeyer flask. The mycelium resuspended in the enzyme solution was incubated at 30° C. on a shaking incubator (Infors) at a low speed (80 rpm) for 1 to 3 h. During the incubation, the formation of the protoplasts was observed under the microscope. Freely moving protoplasts were normally to be seen after 1 h. The end point of the protoplasting was determined by visual inspection under the microscope, and the protoplasts were separated from the remaining mycelium by filtration through glass wool in a glass filter. The glass wool was carefully washed with ice-cold OMT medium. Protoplasts were isolated by centrifuging the suspension in a sterile sample vessel (2 000 rpm; 2 500×g, 4° C., 10 min). Further processing of the cells took place at 4° C. The protoplast pellet was washed by suspension in OMT medium and was reisolated by centrifugation. The washing step was repeated if required. The concentration of protoplasts was determined in a counting chamber under the microscope. The protoplast suspension was adjusted to a concentration of. $1\times10^8$ protoplasts/ml for experiments on protoplast regeneration or for transformations.

For regeneration experiments, serial dilutions were prepared from the protoplast suspension and plated out on agar plates which contained 1.5% malt extract, 0.1% Trypticase peptone, 2% glucose, 1.5% agar and, for osmotic stabilization, 0.4M mannitol. The proportion of viable cells was determined, and the possibility of regenerating the resulting protoplasts to mycelial growth was tested, in this way. In the same way, the proportion of osmotically stable cells (e.g. mycelium fragments) was determined on plates without osmotic stabilizer (without mannitol). The colonies obtained after incubation at 28° C. for 7 days were counted. The proportion of viable cells from a number of protoplast preparations was about 0.5%. These results show that viable and regenerable protoplasts can be produced from *Trametes versicolor* for transformation experiments.

6TH EXAMPLE

Isolation of Uridine-Auxotrophic Mutants of *Trametes versicolor*

Uridine-auxotrophic mutants of *Trametes versicolor* with a gene defect in pyrimidine metabolism (pyr mutants) were isolated by a method based on that described by Boeke et al., Methods Enzymol. (1987) 154, 164–175. The selective agent used was the genotoxic substance 5-fluoroorotic acid (FOA). Mutagenesis of *Trametes versicolor* protoplasts took place by UV treatment.

A: UV Mutagenesis:

The monokaryotic strain *Trametes versicolor* F2 100 described in the 5th example was used for the mutagenesis. Protoplasts of this strain were produced as described in the 5th example.

The UV light source used for the mutagenesis was a BioRad UV linker (BioRad, Munich, power 5.8 W/cm$^2$, distance from the UV source 16 cm). The number of protoplasts used for the mutagenesis was $8 \times 10^9$. Protoplasts of *Trametes versicolor* were placed in a Petri dish and irradiated with UV light for various lengths of time. It emerged from this that, under the described conditions, irradiation for 60 sec was optimal for the subsequent selection of auxotrophic mutants.

B: Selection of Uridine-Auxotrophic Mutants:

The following minimal medium (MM) was used for the selection of uridine-auxotrophic mutants:

| | |
|---|---|
| Glucose | 20 g/l |
| Agar | 15 g/l |
| Potassium dihydrogen phosphate | 1 g/l |
| Magnesium sulfate | 0.5 g/l |
| Disodium hydrogen phosphate | 0.1 g/l |
| Adenine | 27.5 mg/l |
| DL-Phenylalanine | 0.15 g/l |
| L-Asparagine | 2.5 g/l |
| Thiamine | 0.48 mg/l |
| Calcium chloride | 10 mg/l |
| Iron sulfate | 10 mg/l |
| Copper sulfate | 2 mg/l |
| Zinc sulfate | 1 mg/l |
| Manganese sulfate | 1 mg/l |
| pH 5.0, adjusted with sulfuric acid. | |

The MM was supplemented with 0.6M sucrose (MMS) for the osmotic stabilization of protoplasts. For liquid cultures, the MM was prepared without agar.

Initially, the MMS was supplemented with various concentrations of FOA and 10 mM uridine in order to characterize the host properties on selective medium for various *Trametes* strains. It emerged that MMS with 1.5/ml FOA and 10 mM uridine (selective MMS) completely suppressed growth of the *Trametes* strains investigated.

Plates with selective MMS were inoculated with UV-mutagenized protoplasts (described in section A) and incubated at 28° C. for 21 days. In contrast to unmutagenized protoplasts, growth of 35 colonies was observed. These potential pyr-deficient mutants were, in order to characterize the uridine-auxotrophic phenotype in detail, placed on MM plates, MM plates with 10 mM uridine and selective MM plates, and the growth was compared with the F2 100 initial strain. In this, 13 of the 35 picked colonies of *Trametes* mutants unambiguously showed a pyr-deficient phenotype. This is depicted by way of example in table 1 for the wild-type strain and three mutants.

TABLE 1

Growth of Trametes versicolor mutants on various minimal media

| Strain | MM | MM + 10 mM uridine | MM + 10 mM uridine + 1.5 mg/ml FOA |
|---|---|---|---|
| F2 100 | + | + | − |
| F2 100C2-1 | − | + | + |
| F2 100C2-8 | − | + | + |
| F2 100C4-13 | − | + | + |

C: Identification of pyrF Mutants

Mutagenesis with FOA may lead either to mutants in the desired pyrF gene (orotate phosphoribosyltransferase) or in the pyrG gene (orotidine-5'-phosphate decarboxylase). Differentiation of pyrG mutants and pyrF mutants took place by transformation with the pyrF gene from *Trametes versicolor*, isolation of which was described in the 3rd example (plasmid pyrF61). In parallel with this, uridine-auxotrophic *T. versicolor* strains were also transformed with the plasmid pPyrFgap (se 4th example for preparation). Transformation of *Trametes versicolor* is described in the 7th example.

With 6 of the 13 isolated pyr-deficient mutants it was possible to observe colonies on MM after transformation with the plasmids pyrF61 and pPyrFgap. This indicates that these six mutants were deficient in the pyrF gene. The three strains F2 100C2-1, F2 100C2-8 and F2 100C4-13 could be transformed repeatedly with the highest frequency and were used for the subsequent investigations. Comparison of the plasmids pyrF61 and pPyrFgap in relation to transformation frequency showed no significant differences, so that the pyrF promoter was sufficient for isolating transformants.

The pyrF gene described in the 2nd example is a novel selection marker gene for the transformation of *Trametes versicolor*. The strains *Trametes versicolor* F2 100C2-1, F2 100C2-8 and F2 100C4-13 are the first pyrF-deficient strains of *Trametes versicolor* to be described to date. These pyrF-deficient strains can be used as host organisms for the transformation of *Trametes versicolor* and are thus novel and valuable host organisms for protein expression and protein excretion in filamentous fungi from the class Basidiomycetes. The use of the strain F2 100C2-1 for this purpose is described in the following examples.

7TH EXAMPLE

Transformation of pyrF-Deficient *Trametes versicolor* Strains with the pyrF Gene From *Trametes versicolor*

A: Isolation of Transformants

Protoplasts of *T. versicolor* F2 100C2-1 were produced by the method described in the 5th example. In this case, the culture medium for the auxotrophic strain was supplemented with 10 mM uridine. Transformation was carried out with the vector pyrF61 (described in the 3rd example) or pPyrFgap (described in the 4th example).

Protoplasts were produced from *Trametes versicolor* F2 100C2-1 as described in the 5th example and were suspended in a final concentration of $10^8$/ml. 0.1 ml aliquots of the protoplasts were mixed in each case with 10 µg of DNA of the relevant plasmid in incubation vessels with a volume of 12 ml and incubated on ice for 30 min. After this, 1.25 ml of a PEG4000 solution was added slowly and with repeated mixing to the transformation mixture. After incubation at room temperature for a further 20 min, the reaction vessels were filled with the OMT medium described in the 5th example, mixed and centrifuged at 2 000×g and 4° C. for 10 min. The pellets were resuspended and plated out on osmotically stabilized MMS plates without uridine (described in the 6th example). The plates were incubated at 28° C. for 14 days and checked for growth of colonies. Transformation rates of 0.5–3 transformants/µg of plasmid DNA were achieved in various experiments.

B: Purification of the Transformants

Mycelium of the resulting transformants was picked and purified by plating out on fresh MM plates. The inoculum was applied as a spot in the middle of the plate in this case. After incubation at 28° C. for about 7 days, radial mycelial growth was observable. This purification process was repeated, taking the mycelium for the inoculum from the edge of the first purification plate. MM plates were then reinoculated with inoculum from the second purification plate and incubated at 28° C. until the plates were completely covered with mycelial growth.

C: Analysis of the Transformants

Transformants of *Trametes versicolor* were investigated by Southern blot analysis for integration of the plasmid pyrF61. This was done by producing mycelium of various transformants and, as a control, the pyrF-deficient strain F2 100C2-1 in liquid culture (see 2nd example, malt extract medium, with addition of 10 mM uridine for F2 100C2-1). Chromosomal DNA was isolated from the isolated mycelium as described in the 2nd example.

3 µg of chromosomal DNA from each of the investigated transformants and the untransformed, uridine-auxotrophic F2 100C2-1 initial strain, and 100 ng of the plasmid pyrF61 were cut with Nco I and then separated by agarose gel electrophoresis and blotted onto nylon filters (Qiagen). The DNA probe used was Nco I-cut plasmid pyrF61, nonradiolabeled as described in the 1st example. It was possible to detect with this DNA probe both the pyrF gene and the vector portions from the respective plasmid.

The temperature for the hybridization of the DNA blotted onto nylon filters with the unradiolabeled DNA probe was 60° C. Otherwise, the conditions described in the specialist literature for Southern blots were complied with. Southern blots were analyzed by autoradiography. Besides other fragments, it was possible to detect two Nco I fragments which were derived from the pBK CMV vector portion of pyrF61 and had a length of 0.7 kb and 1.9 kb respectively. These two fragments were detectable only in the transformants but not in the uridine-auxotrophic strain F2 100C2-1. This result confirms that on transformation of the uridine-auxotrophic *Trametes versicolor* strain F2 100C2-1 the plasmid pyrF61 had been integrated into the genome and led to productive expression of the selection marker gene pyrF, whereby the uridine auxotrophy of this strain was complemented.

8TH EXAMPLE

Use of the pyrF Gene for Producing Laccase-Overproducing *Trametes versicolor* Strains A. Transformation of *T. versicolor*

Protoplasts of *T. versicolor* were produced by the process described in the 5th example. The vector pyrF61 described in the 3rd example, and the laccase expression vector pLac3gap were used for the transformation. The two vectors were used in cotransformation experiments where the selection marker gene and the gene to be expressed were present on separate plasmids. The production of pLac3gap was disclosed in DE-A-19814853, 6th example. In pLac3gap, the gene for laccase III from *T. versicolor* is functionally linked to the GAPDH promoter from *T. versicolor*.

Protoplasts of the pyrF-deficient strain *Trametes versicolor* F2 100C2-1 were produced as described in the 7th example and were suspended in a final concentration of $10^8$/ml. 0.1 ml aliquots of the protoplasts were mixed with 10 µg of DNA of each of the plasmids pLac3gap and pyrF61 in incubation vessels with a volume of 12 ml and incubated on ice for 30 min. After this, 1.25 ml of a PEG4000 solution was added slowly and with repeated mixing to the transformation mixture. After incubation at room temperature for a further 20 min, the reaction vessels were filled with the OMT medium described in the 5th example, mixed and centrifuged at 2 000×g and 4° C. for 10 min. The pellets were resuspended and plated out on osmotically stabilized MM without uridine (described in the 6th example). The plates were incubated at 28° C. for 14 days and examined for growth of colonies. Transformation rates of 0.5–3 transformants/µg of DNA of the selection marker plasmid pyrF61 were achieved in various experiments.

The resulting transformants were picked and purified twice as described in the 7th example by plating out on fresh plates with MM selection medium without uridine. Selective plates were then inoculated anew with inoculum from the second purification plate and, after the plates were completely covered with mycelial growth the laccase production was checked in shaken flask cultures.

B: Culturing in a Shaken Flask

For culturing in a shaken flask, 2 cm$^2$ of mycelium were punched out of a plate showing full growth and were crushed under sterile conditions and used to inoculate a preculture of 50 ml (in a 250 ml Erlenmeyer flask) of malt extract medium (see 1st example). The preculture was incubated at 28° C. while shaking at 120 rpm for 6 days. On the sixth day, the preculture was homogenized with an Ultra Turrax at 9 500 rpm for 30 sec and used to inoculate 250 ml of main culture medium (for composition, see MM in the 6th example) in a 1 l Erlenmeyer flask. The main culture was then again incubated at 28° C. while shaking at 120 rpm. Laccase production was measured each day starting on the second day of culturing. Laccase activity was measured by photometry using the substrate ABTS (2,2'-azinobis(3-ethylbenzothiazoline-6-sulfonic acid)) at 420 nm. (Extinction coefficient of ABTS at 420 nm $\epsilon_{420}$: $3.6 \times 10^4 [1 \times mol^{-1} \times cm^{-1}]$. In this, 1U of laccase activity corresponded to the conversion of 1 µmol of ABTS/min at 37° C. and a pH of 4.5. The maximum laccase production in shaken flask cultures was reached 10–14 days after starting the main culture. Table 2 shows a comparison of various transformants with the untransformed starting strain *Trametes versicolor* F2 100. For the untransformed strain F2 100, laccase production was additionally determined after induction with the inducer 2,5-xylidine described in the literature (Yaver et al., Applied and Environmental Microbiology (1996) 62, 834–841). As is evident from table 2, laccase production in a shaken flask was increased with the best transformants of the strain F2 100 by a factor of 14 (without induction) and by a factor of 6 (with induction) compared with the untransformed starting strain.

TABLE 2

| Trametes versicolor strain | Maximum laccase production (U/ml) |
|---|---|
| F2 100 | 4.60 |
| F2 100/xylidine* | 11.20 |
| TV L3F-4 | 15.20 |
| TV L3F-7 | 42.50 |
| TV L3F-9 | 17.60 |
| TV L3F-14 | 51.50 |
| TV L3F-21 | 33.90 |
| TV L3F-29 | 64.80 |
| TV L3F-35 | 35.10 |
| TV L3F-35 | 13.80 |
| TV L3F-51 | 56.70 |

*Induction took place three days after starting the main culture by adding 2,5 xylidine (final concentration 1.5 mM).

The invention claimed is:

1. An isolated DNA sequence which codes for a protein having an enzymatic activity of orotate phosphoribosyltransferase (pyrF activity) which comprises:
a DNA sequence selected from the group consisting of:
the DNA sequence SEQ ID NO: 1 from position 1133 up to and including position 1877; and
the DNA sequence SEQ ID NO: 2 in from position 1 up to and including position 684.

2. An isolated protein having pyrF activity, which comprises:
an amino acid sequence SEQ ID NO: 3.

3. An expression vector which comprises the DNA sequence as claimed in claim 1.

4. A transformed microorganism which comprises the expression vector as claimed in claim 3.

5. A process for producing a pyrF protein, which comprises cultivating in a culture a microorganism comprising the vector of claim 3; and obtaining the protein from the culture.

* * * * *